(12) United States Patent
Hochkoeppler et al.

(10) Patent No.: US 8,557,267 B2
(45) Date of Patent: Oct. 15, 2013

(54) METHOD FOR PREVENTING AND CONTROLLING BIOFOULING ON MARINE OBJECTS

(75) Inventors: Alejandro Hochkoeppler, Bologna (IT); Lucio Panizza, Bologna (IT); Elena Roda, Bologna (IT); Alessandra Stefan, Bologna (IT)

(73) Assignee: Archimede R&D S.R.L., Bologna (IT)

( * ) Notice: Subject to any disclaimer, the term of this patent is extended or adjusted under 35 U.S.C. 154(b) by 0 days.

(21) Appl. No.: 13/261,007

(22) PCT Filed: May 19, 2010

(86) PCT No.: PCT/EP2010/056870
§ 371 (c)(1),
(2), (4) Date: Nov. 14, 2011

(87) PCT Pub. No.: WO2010/145905
PCT Pub. Date: Dec. 23, 2010

(65) Prior Publication Data
US 2012/0064026 A1 Mar. 15, 2012

(30) Foreign Application Priority Data
May 22, 2009 (IT) .............................. BO2009A0333

(51) Int. Cl.
*A01N 25/24* (2006.01)
(52) U.S. Cl.
USPC ........................................................ 424/407
(58) Field of Classification Search
None
See application file for complete search history.

(56) References Cited

U.S. PATENT DOCUMENTS

| 3,915,853 | A | * | 10/1975 | Luck | 210/606 |
|---|---|---|---|---|---|
| 5,717,007 | A | * | 2/1998 | Cambon | 523/122 |
| 5,770,188 | A | | 6/1998 | Hamade et al. | |
| 5,876,990 | A | * | 3/1999 | Reddy et al. | 435/177 |
| 2003/0166237 | A1 | * | 9/2003 | Allermann et al. | 435/204 |
| 2005/0147579 | A1 | | 7/2005 | Schneider et al. | |

FOREIGN PATENT DOCUMENTS

| WO | WO 96/08967 A1 | 3/1996 |
|---|---|---|
| WO | WO 02/099026 A1 | 12/2002 |

OTHER PUBLICATIONS

Olsen et al:"Enzyme-based antifouling coatings" Biofouling (Chur), Harwood Academic Publishers, Chur, CH, vol. 23, No. 5/6, Jan. 1, 2007, pp. 369-383, XP009137736.
Verpoorte J A et al:"Esterase activities of human carbonic anhydrases B and C", Journal of Biological Chemistry, American Society for Biochemistry and Molecular Biolog, US, (Sep. 1967).

* cited by examiner

*Primary Examiner* — Carlos Azpuru
(74) *Attorney, Agent, or Firm* — Modiano & Associati; Daniel O'Byrne; Albert Josif

(57) ABSTRACT

A method for preventing and controlling the formation of biofouling on an object that is immersed or partially immersed in a water environment in which there is one or more organic or inorganic compounds capable of releasing gas, comprising the step of applying to the surface of the object a composition comprising a polymeric resin and one or more enzymes or a paint or a coating and one or more enzymes, wherein the one or more enzymes are adapted to catalyze a reaction of the one or more compounds that leads to the formation of gas.

14 Claims, No Drawings

METHOD FOR PREVENTING AND CONTROLLING BIOFOULING ON MARINE OBJECTS

The present invention relates to a method for preventing and controlling the biofouling phenomenon.

BACKGROUND OF THE INVENTION

Biofouling is a known phenomenon and has been investigated for a long time, which consists in the sedimentation of different species of organisms (from single proteins to microorganisms like bacteria and protozoans, to complex macroorganisms like serpulids and bryozoans) on artificial substrates that are immersed in water environments. Typically, the biofouling phenomenon takes place on substrates placed in water environments, with the consequential technological alteration of the objects: already after an hour of immersion, an initial film consisting of bacteria and other microorganisms begins to form on the hull of a boat; biofouling has, over time, negative repercussions in various nautical fields, like commercial boating, pleasure boating, and competitive boating. The organisms that constitute the biofouling, in fact, lead to deterioration, discoloring and corrosion of the objects subject to biofouling, with the subsequent loss of performance, and increase in the fuel consumption. To avoid the problems caused by the aesthetic and structural decline of the objects placed in direct contact with the water environment, repeated treatments and laying ups on the abovementioned objects are necessary.

The most efficient system to fight against biofouling is to apply antifouling paint directly on the products subject to biofouling. The first formulations of these paints, going back to the 60's, are based on products that are self-smoothing with an organostannic polymeric matrix. The objects treated with these formulations slide well in the water, at the expense of having, however, a high environmental impact. In fact, these paints typically contain tributyltin (TBT); this chemical compound is highly toxic: the TBT-based biocides accumulate in the sediments and in the food chains, which irreversibly modify the various ecosystems. The introduction of some community laws tried to hold this environmental problem in check, by imposing the use of other organometallic and organic biocide based paints.

Currently numerous patents exist regarding eco-compatible antifouling paints based on other types of biocide; however, all these products have intrinsic and evident deficiencies in performance and/or durability. For example, the self-smoothing (or hydro-erodible) paints and the "hybrid" paints, or rather the self-smoothing/releasing antifouling chemicals that are not specifically biocides, are lacking in performance because the antifouling coating has a short duration, and are not easily predictable/controllable as a function of the variability of the environmental conditions of the waters and the work regime.

The paints containing organic biocides that don't damage (or claimed as to be not damaging) the water environment, not only have a progressive loss in coating efficiency and are not easily controllable like for the self-smoothing paints, but also show important hygienic and environmental implications; in fact, these products have eco-effects that have not been sufficiently studied and/or known over long term, and potential health risks for the operators during the step of manipulating the product.

The chemically inert or bio-inert paints with a low surface tension are instead perfectly eco-compatible, but do not adhere well to the substrates to which they are applied, and have a reduced mechanical resistance and resistance to abrasion.

Finally, the chemically inert and bio-inert paints with a very low surface tension with a diversified polymeric nature and partially fluorized, show good efficiency, but poor durability due to lacking cohesiveness and poor adhesiveness of the coating to the majority of substrates.

Currently, different types and brands of antifouling products can be found on the market, which are all based on a formulation of the film that is able to dissolve biologically active chemical compounds in water. The toxicity of these chemical compounds is able to inhibit fouling on the immersed structures, by efficiently repelling or killing settled organisms.

Substantially, there are three forms of biocide release:
1. release due to hydration;
2. release due to erosion;
3. release due to hydrolytic degradation of the matrix.

Depending on the type of boat and/or object that is immersed, its use, and the quality of the water in which it is allocated and/or in which it has its principal use, four types of biocide paints can be identified:
1. traditional paints with a soluble matrix, wherein the biocide release occurs due to the erosion of the bonding polymer;
2. paints with a partially soluble matrix (long-life), wherein the biocide release occurs due to the hydration and erosion of the film;
3. paints with a hard or insoluble matrix, wherein the biocide release occurs due to hydration;
4. self-smoothing or self-polishing paints, wherein the biocide release occurs due to the hydrolytic degradation of the matrix.

All of these paints contain biocides that are different from the tributyltin compounds, in which copper based compounds play an important role, but these are also intrinsically damaging to the environment, though less so than compared to TBT-based products. For this reason, it is highly probable that these biocides, which are commonly used today, will be banned or their use limited in the near future through community or world-wide laws.

For all of the reasons mentioned above, an eco-compatible method for preventing and controlling the formation of biofouling that occurs in water environments and which avoids the use of products which are dangerous to the environment (with the possibility of being against the current laws regarding biocides) is highly desirable.

SUMMARY OF THE INVENTION

The aim of the present invention is to provide a method for preventing and controlling the formation of biofouling on objects that are immersed or partially immersed in a water environment which does not use TBT or other biocide compounds that are dangerous to the environment.

This aim is achieved by a method for controlling and preventing the formation of biofouling on an object that is immersed or partially immersed in a water environment in which there is one or more organic or inorganic compounds capable of releasing gas, comprising the step of applying to the surface of said object a composition comprising a polymeric resin and one or more enzymes or a paint and/or a coating and one or more enzymes, wherein the one or more enzymes are adapted to catalyze a reaction of said one or more compounds that leads to the formation of gas.

Further characteristics and advantages of the invention will become better apparent from the following detailed description of a preferred but not exclusive embodiment of the method for preventing and controlling the formation of biofouling.

DESCRIPTION OF THE PREFERRED EMBODIMENTS

An innovative method has been developed for the prevention and control of biofouling on an object that is immersed or partially immersed in a water environment in which there are one or more organic or inorganic compounds capable of releasing gas, comprising the step of applying to the surface of said object a composition comprising a polymeric resin and one or more enzymes or a paint and/or coating containing one or more enzymes, wherein the one or more enzymes are adapted to catalyze a reaction of said one or more compounds that lead to the formation of gas. The immersed or partially immersed object can be static or non-static, including any kind of floating object moved by an engine or other types of propulsion, such as for example, a sail, pedals, oars. The water environment can be of different nature, for example marine, lake or river environments. This eco-compatible product is based on the use of formulations containing enzymes, which have characteristics that have a low environmental impact and are eco-compatible with the water systems. Said method takes advantage of gas derived after the catalyzed reactions by the enzymes, to create a kinetic action that prevents and controls the biofouling. The method for preventing and controlling the formation of biofouling according to the present invention provides for the application on the surface of an object that is immersed or partially immersed in a water environment, whether it is a closed basin or an open system, of a composition comprising a polymeric resin that is functionalized with one or more enzymes capable of catalyzing reactions based on organic or inorganic substrates, which are present in said water environments, that can release gas. In particular, the product is set up as a preparation that can be applied on objects placed in water environments, which constantly has, though in variable concentrations, compounds with the generic formula (M)x(XOz)y where X=C, N, S, O, P, H, Br, Cl, B, F and where M is a metallic ion or a cationic entity and where X, y, z are charges such that the salt has a neutral charge and is balanced; typically, these compounds are carbonated salts, phosphates, nitrites, nitrates, sulfites and sulfates. In this way the enzyme reaction that breaks the chemical bonds and releases gas hi the water environment is possible; the effervescence released leads to turbulence on the surface of the immersed or partially immersed object, which in this way inhibits and opposes the formation of biofouling on said object.

In other words, the products of the enzyme-organic/inorganic compound reaction create a continuous effervescence that creates a motion that slows down and/or reduces the formation of biofouling. The formulation, therefore, is not based on the typically determined biocides, but on the physical movement created by the gas of the reaction. Advantageously, the direct application of the composition on the surfaces to be treated allows for the efficiency of the formulation to be localized and concentrated only on the areas affected by biofouling. Further, such gases can have biocide effects on the organisms that compose the biofouling that has possibly formed on the surface of the object, without having any significant eco-toxicological effects at the same time.

Preferably, the enzymes that are capable of catalyzing such reactions are selected from the group consisting of oxidoreductases, lyases and hydrolases.

In a preferred embodiment, the enzymes that belong to the lyases class belong to the subclass of the carbonic anhydrases, more preferably the bovine carbonic anhydrases. The use of these enzymes, which are particularly adapted to the water environments due to the natural presence of carbonated salts, leads to the production and release of gas, such as $CO_2$, whose release in the waters surrounding the surface of the object on which the composition has been applied allows for the formation of biofouling to be slowed down and prevented, as described above. It is clear, therefore, that the efficiency of the product does not depend exclusively on the toxicity of the active ingredient, but on the variable concentration of salts present in the waters; such concentration can be adjusted with the addition of particular additives to the product. This characteristic allows the product to be compatible with the more various geographic regions in the world.

Preferably, the quantity of active enzymes, expressed in the percentage w/w, which are capable of catalyzing the abovementioned reactions is comprised in the range 0.001-30%; in particular, the quantity of active enzymes is comprised in the range 0.06-3% w/w. Preferably, the quantity of active enzymes is comprised in the range 0.06-0.1% w/w. In other words, the quantity of enzymes capable of catalyzing the abovementioned reactions is comprised in the range 3000-1500000 $U/m^2$ of surface to be treated, preferably 11000-80000 $U/m^2$ of surface to be treated; even more preferably the quantity of enzymes is comprised in the range 10000-70000 $U/m^2$.

The active enzyme is defined as the enzyme that maintains its ability to transform the substrate. The active enzyme carries out its function of accelerating the speed of the reaction and it therefore reaches the state of thermodynamic equilibrium more quickly.

The enzyme carries out its function by facilitating the reactions through the interaction between the substrate (the molecule or the molecules that participate in the reaction) and its own active site (the part of the enzyme where the reactions occur), forming a complex. Once the reaction has occurred, the product is moved away from the enzyme, which remains available to start a new one. The enzyme in fact is not consumed during the reaction.

The enzyme is defined as active when it is capable of transforming at least one molecule of the substrate in a set time under certain experimental conditions.

Preferably, in the case that the carbonic anhydrases are used, the biocatalyzed organic compounds are characterized by the fact that they have one or more functional groups that are selected from the group of organic compounds that have the generic structure R-XOz-R1, wherein:

i) said organic compounds can be sources of H+ ions;
ii) X is selected from the group consisting of C, N, S, O, P, Cl, B, F, Br;
iii) z assumes a numeric value comprised in the range 1-4;
iv) R and R1 are selected from the group consisting of hydrogen, saturated hydrocarbon groups, unsaturated hydrocarbon groups, ramified hydrocarbon groups, or linear hydrocarbon groups, and wherein said R1 may not be present in the structure.

In other words, the functional groups of the abovementioned generic structure are selected preferably from the group consisting of carboxyl groups, carbonyl groups, acetal groups, ketal groups and their combinations.

Preferably, in the case that the carbonic anhydrases are used, the biocatalyzed inorganic compounds are carbonated salts, salt nitrites, nitrates, phosphates, phosphites, sulfates, sulfites, which is a constant characteristic, even if with different concentrations, above all in the water environments.

In a preferred embodiment, the composition further comprises one or more organic or inorganic compounds capable of releasing gas following the reaction catalyzed by said one or more enzymes on said one or more compounds.

Preferably, the method which uses carbonic anhydrases can further comprise a source added of $CO_2$. In this way the enzymatic catalysis of the carbonic anhydrases is favored toward the formation of $CO_2$.

Preferably, the sources added of $CO_2$ are selected from the group of inorganic salts consisting of salts containing chlorine, sodium, magnesium, sulfur, calcium, potassium, bromine, carbon, strontium, boron, silicon, fluorine, argon, and nitrogen, or from the group of organic compounds consisting of substances containing acetate groups and/or ester bonds.

The substances produced by the reactions catalyzed by the enzymes can also be other gaseous substances including for example nitrogen and its nitric oxides, sulfuric oxides, oxides of phosphorus and hydrogen, oxygen. In this case the sources of such substances are the relative inorganic salts such as nitrites, nitrates, sulfites, sulfates, phosphites, phosphates and sources of $H^+$ ions.

In a preferred embodiment, the polymers that constitute the polymeric resins are selected from the group consisting of epoxy polymers, vinyl polymers, acrylic polymers, polymers of the polysiloxane type, comprising final products with a hybrid lattice structure of the IPN type which derive from multifunctional reactive compounds that include epoxies, (meth)acrylics, vinyls, homopolymers and copolymers with a high molecular weight that carry fluoroalkyl side chains and/or chemical groups, like copoly(meth)acrylates that carry perfluoroalkyl or oxialkyl side chains which are bonded by means of ester or urethane groups, partially fluorized polyvinylesters and polyurethanes, copolymers of the polysiloxane type, which contain or carry fluoroalkyl groups or sequences, methyl methacrylate (MMA) copolymers.

In a preferred embodiment, the polymeric resin has a lattice structure that comprises internally one or more enzymes that are functionalized by means of covalent bonds, ion bonds and other types of chemical interactions. The product may already contain the polymerized polymeric matrix or the formation of the lattice structure may occur after the application of the paint on the surface of the object that will be immersed in water. In both cases the enzyme remains blocked within the matrix. Such lattice structure will have the characteristic that it leaves the active part of the enzyme free, so that the active part can come in contact with the substrates to catalyze the reaction of producing $CO_2$ and other gaseous substances from substances that are present in the water. In the case of matrix trapping, that is a known technique of enzymatic immobilization which is subsequently described along with other enzymatic immobilization techniques, such process can occur in particular during the step of applying the antifouling product, while the capsule enzyme can in particular be dissolved in the product, which will then be applied to the surface of the object.

In this way the reticulated resins allow for the passage of water molecules, of organic and inorganic compounds, and of gases released from the enzymatic catalysis. The main advantage of this immobilization technology is that the method found with the present invention can be used without varying the methods and applied technologies which are already known.

In a preferred embodiment, the polymeric resin that is functionalized with one or more enzymes comprises a layer of resin on the surface of which one or more enzymes are functionalized by means of chemical bonds. The immobilization of the enzymes occurs through the bond of the enzyme at its non-active part with a substrate. In this way the enzyme is not free, but at the same time is capable of being active in its function as a catalyst. The enzyme thus bonded will be inserted in the paint and the substrate to which it is anchored will allow such enzyme to be bonded to the surface of the applied paint, in such a way as to carry out its function towards the substrates present in the water being used. This type of product, which differs from the preceding enzymatic immobilization, has a modification to the applied strategies, since a technique with two steps is used (first the resin and then the active element); however, this technology is advantageous because the enzyme that is applied on the surface is in direct contact with the water environment, which allows it to carry out its function even more.

Another aspect of the present invention relates to an enzymatic composition for preventing and controlling biofouling, said enzymatic composition consisting of immobilized enzymes on resins according to the techniques of entrapment, or the functionalization of the resin with one or more enzymes through chemical interactions.

The enzymatic compositions of the present invention can be prepared with enzymatic immobilization techniques that are well known and investigated in the literature. All these enzymatic immobilization techniques have different applications, but have never been used in the biofouling field.

A typical form of enzymatic immobilization is the entrapment. This methodology is based on the localization of the enzyme within a lattice structure, a polymer matrix or a membrane. The system allows for the holding of the enzyme and at the same time for the penetration of the substrate. This technique can be classified under the following types:

1) lattice;
2) microencapsulation.

The entrapment method varies as a function of the type of enzyme. In the lattice method the enzyme is entrapped within the interstitial spaces of a polymer that has cross-linking bonds that are insoluble in water. Some synthetic polymers, including polyacrylamide, polyvinyl alcohol and, in some cases, starch, are used to immobilize the enzyme with this technique.

The microencapsulation method consists in entrapping the enzyme within the semi-impermeable polymeric membrane; the microencapsulation methods can be classified as:

1) method of interfacial polymerization: a mixture of the enzyme and a hydrophilic monomer are mixed within a solvent which is not miscible with water. The polymerization of the monomer occurs in the interface of the two phases (solvent-water);

2) liquid drying: a polymer is dissolved in an organic solvent which is not miscible with water. A water solution of the enzyme is dispersed in the organic phase, initially forming an emulsion of the oil-water type. This emulsion is then dispersed in a water phase which contains protective colloidal substances including gelatin, and surface-active agents; a second emulsion is thus prepared. The organic solvent is therefore removed. A polymeric membrane is finally produced to give microcapsule enzymes;

3) separation of phases: consists in the solution of the polymer in an organic solvent and its reprecipitation. This aim is achieved with the addition of another organic solvent which is miscible with the first one, but in which the polymer is not miscible.

The solid supports used with these techniques can be organic or inorganic. Some solid supports can include:

polysaccharides, proteins, carbons, polystyrenes, polyacrylates, maleic anhydride based copolymers, polypeptides, vinyl and allyl and polyamide polymers.

Other known methods of enzymatic immobilization are:

Carrier-Binding: with this technique the enzyme bonds to a substrate that is insoluble in water; the choice of the substrate depends on the physical chemical properties, the molecular dimensions of the enzyme, the chemical composition and the relationship between hydrophilic and hydrophobic groups. Based on the type of bond used the carrier binding can be further divided in other subclasses: Physical Absorption, Ionic Binding, and Covalent Binding.

Cross-Linking: relates to an intramolecular cross-linking of the enzyme through bifunctional or multifunctional reagents; such technology is applied through the intramolecular bond with other proteins, but what is more interesting is the bond with functional groups of insoluble matrices.

The enzymatic preparation of the present invention can be applied on static or non-static objects, which are immersed or partially immersed in water environments, and belong to, for example, to the category of sailboats, motorboats, steamboats, rowboats, or boats which are propelled manually. Following are some non-exhaustive illustrative examples which pertain to the present invention.

EXAMPLES

Example 1

Below are some formulations of the product:
Formulation 1

| Ingredient | Quantity (% w/w) |
|---|---|
| Epoxy resin | 20 |
| Organic solvent | 50 |
| Antioxidant (ascorbic acid) | 5 |
| Enzyme | 3 |
| Colour (metal oxide, Fe, Cu, etc.) | 5 |
| Dodecyl-dimethyl-dichlorobenzyl-Ammonium chloride | 10 |
| Methoxy propanol | 7 |

Formulation 2

| Ingredient | Quantity (% w/w) |
|---|---|
| Acrylic resin | 30 |
| Acetate solvent | 55 |
| Antioxidant | 3 |
| Enzyme | 1 |
| Colour (metal oxide, Fe, Cu, etc.) | 2 |
| Calcium carbonate | 9 |

Formulation 3

| Ingredient | Quantity (% w/w) |
|---|---|
| Enzyme | 0.5 |
| Silicone resin | 50 |
| Solvent of Dibasic esters | 30 |
| Mixture of Bis (1,2,2,6,6-Pentamethyl-4-piperidyl) sebacate and Methyl 1,2,2,6,6-pentamethyl-4-piperidyl sebacate | 1.5 |
| Silicon oxide | 1.5 |
| Fe carbonate | 10 |
| Titanium oxide | 8 |

Formulation 4

| Ingredient | Quantity (% w/w) |
|---|---|
| Enzyme | 3 |
| Acrylic resin | 40 |
| Dibasic esters | 30 |
| Zinc oxide | 15 |
| Mixture of triphenyl phosphate propylate | 5 |
| Magnesium carbonate | 7 |
| Bentonite | 5 |
| Mixture of isoparaffin solvents | 2 |

Example 2

Enzyme tested in seawater environment (collected from the Emilia Romagna coast), with the addition of a buffer of Trisulfate 15 mM pH 7.6:

carbonic anhydrases from bovine erythrocytes (stock 0.04%, 1000 U/mL)

Concentration of enzyme in seawater:

50 units of enzyme (final concentration 0.002%)

The activity was determined in two ways:

1) degradation of the substance p-nitrophenyl acetate, determined through the measurement of the variation in the absorbance of such substance at 348 nm;

2) determination of the product of $CO_2$ of a solution of seawater containing the enzyme compared to a solution of the same in demineralized water.

Results

1) Concentration of the enzyme in seawater 50 units of enzyme (final concentration 0.002%)

Activity after 10 Minutes

| Buffer (−enzyme) | Seawater (−enzyme) |
|---|---|
| 0 | 0.0012 |

| Buffer (+enzyme) | Seawater (+enzyme) |
|---|---|
| 0.0678 | 0.0330 |

Activity After 1 Hour

| Buffer (+enzyme) | Seawater (+enzyme) |
|---|---|
| 0.0643 | 0.0363 |

Activity After 15 Hours

| Buffer (+enzyme) | Seawater (+enzyme) |
|---|---|
| 0.0518 | 0.0291 |

In terms of percentage compared to the ideal solution (no seawater):
Enzyme activity after 10 minutes: 48.67%
Enzyme activity after 1 hour: 56.45%
Enzyme activity after 15 hours: 56.17%

2) Determination of the capability of the enzyme to produce $CO_2$ from seawater. This can be measured through Gas Chromatography (GC). The reaction of the dehydration is favored compared to the inverse reaction in a solution with pH between 5.5 and 7.5. The formation of $CO_2$ was measured 5 minutes after the addition of the enzyme, injecting $500^2$ μL of air present in the headspace in the GC.

Final concentration of enzyme 0.06%, 5000 units
Seawater Environment with the Addition of a Buffer of Tri-HCl 0.1 M pH 7.2 and Carbonate Solution

|  | Peak area | Percentage (%) |
|---|---|---|
| Ideal system (−) | 41561 | 0.62 |
| Seawater (−) | 49298,0 | 0.73 |
| Ideal system (+E) | 142575 | 2.12 |
| Seawater (+E) | 119032 | 1.77 |

The production of $CO_2$ in the seawater where the enzyme is present is 2.42 times greater than in the seawater without the enzyme.

The disclosures in Italian Patent Application No. BO2009A000333 from which this application claims priority are incorporated herein by reference.

The invention claimed is:

1. A method for controlling formation of biofouling on an object that is immersed or partially immersed in a water environment in which there is one or more organic or inorganic compounds capable of releasing $CO_2$, comprising the step of applying to the surface of said object a composition comprising a polymeric resin and one or more enzymes or a paint and/or a coating and one or more enzymes, wherein the one or more enzymes are adapted to catalyze a reaction of one or more organic or inorganic compounds that leads to the formation of $CO_2$, wherein the quantity of enzymes capable of catalyzing the reactions is comprised in the range 0.001-30% w/w and wherein the one or more enzymes are lyases that belong to the subclass of carbonic anhydrases.

2. The method according to claim 1, wherein the carbonic anhydrases are bovine carbonic anhydrases.

3. The method according to claim 1 wherein the quantity of enzymes capable of catalyzing the reactions is comprised in the range 0.06-3% w/w, preferably 0.06-1% w/w.

4. The method according to claim 1, wherein the composition further comprises a source of $CO_2$.

5. The method according to claim 1, wherein the polymers that constitute the polymeric resin are selected from the group consisting of epoxy polymers, acrylic polymers, (meth) acrylic polymers, vinyl polymers, polysiloxanes, homopolymers and copolymers with a high molecular weight that carry fluoroalkyl side chains and/or chemical groups.

6. The method according to claim 1, wherein the polymeric resin functionalized with one or more enzymes has a lattice structure that comprises internally the one or more enzymes bonded by means of covalent bonds, ion bonds and other types of chemical interaction.

7. The method according to claim 1, wherein the polymeric resin functionalized with the one or more enzymes consists of a layer of resin on the surface of which the one or more enzymes are bonded by means of chemical bonds.

8. A method for controlling formation of biofouling on an object that is immersed or partially immersed in a water environment in which there is one or more organic or inorganic compounds capable of releasing $CO_2$, comprising the step of applying to the surface of said object a composition comprising a polymeric resin and one or more enzymes or a paint and/or a coating and one or more enzymes, wherein the one or more enzymes are adapted to catalyze a reaction of one or more organic or inorganic compounds that leads to the formation of $CO_2$, wherein the quantity of enzymes capable of catalyzing the reactions is comprised in the range 0.001-30% w/w and wherein the composition further comprises a source of $CO_2$.

9. The method according to claim 8, wherein the one or more enzymes are lyases that belong to the subclass of carbonic anhydrases.

10. The method according to claim 9, wherein the carbonic anhydrases are bovine carbonic anhydrases.

11. The method according to claim 8, wherein the quantity of enzymes capable of catalyzing the reactions is comprised in the range 0.06-3% w/w, preferably 0.06-1% w/w.

12. The method according to claim 8, wherein the polymers that constitute the polymeric resin are selected from the group consisting of epoxy polymers, acrylic polymers, (meth) acrylic polymers, vinyl polymers, polysiloxanes, homopolymers and copolymers with a high molecular weight that carry fluoroalkyl side chains and/or chemical groups.

13. The method according to claim 8, wherein the polymeric resin functionalized with one or more enzymes has a lattice structure that comprises internally the one or more enzymes bonded by means of covalent bonds, ion bonds and other types of chemical interaction.

14. The method according to claim 8, wherein the polymeric resin functionalized with the one or more enzymes consists of a layer of resin on the surface of which the one or more enzymes are bonded by means of chemical bonds.

* * * * *